(12) United States Patent
Buccellato et al.

(10) Patent No.: US 11,584,558 B2
(45) Date of Patent: Feb. 21, 2023

(54) SHRINK-FORMED PACKAGE

(71) Applicant: Medtronic Vascular, Inc., Santa Rosa, CA (US)

(72) Inventors: James T. Buccellato, Blaine, MN (US); Jeffrey B. Barnell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 279 days.

(21) Appl. No.: 16/218,112

(22) Filed: Dec. 12, 2018

(65) Prior Publication Data
US 2020/0189781 A1   Jun. 18, 2020

(51) Int. Cl.
| B65B 53/06 | (2006.01) |
| B65B 55/18 | (2006.01) |
| B65B 63/08 | (2006.01) |
| B65D 75/00 | (2006.01) |

(52) U.S. Cl.
CPC ........... *B65B 53/06* (2013.01); *B65B 55/18* (2013.01); *B65B 63/08* (2013.01); *B65D 75/002* (2013.01)

(58) Field of Classification Search
CPC ......... B65B 53/06; B65B 55/18; B65B 63/08; B65D 75/002
USPC ........................................................ 53/442
See application file for complete search history.

(56) References Cited

U.S. PATENT DOCUMENTS

| 4,321,781 A * | 3/1982 | Hall .................. A61F 2/0095 |
| | | 53/427 |
| 6,161,695 A * | 12/2000 | Nicolais .............. B65B 31/00 |
| | | 53/434 |
| 2005/0268573 A1 | 12/2005 | Yan |
| 2008/0202961 A1 | 8/2008 | Sharp |
| 2013/0272630 A1 | 10/2013 | Thomas et al. |
| 2014/0202117 A1 * | 7/2014 | Newell ................ B65B 53/066 |
| | | 53/442 |
| 2016/0137328 A1 * | 5/2016 | Paynter ............... B65B 53/066 |
| | | 53/442 |
| 2016/0347492 A1 | 12/2016 | Lu et al. |

FOREIGN PATENT DOCUMENTS

| JP | 2004051175 | 2/2004 |
| WO | 2017010577 A2 | 1/2017 |

OTHER PUBLICATIONS

EP19213590.3, Extended European Search Report, dated May 8, 2020, 9 pages.

* cited by examiner

*Primary Examiner* — Valentin Neacsu
*Assistant Examiner* — Mary C Hibbert-Copeland
(74) *Attorney, Agent, or Firm* — Shumaker & Sieffert, P.A.

(57) ABSTRACT

An example technique of forming a package includes retaining a package precursor in a support. The package precursor includes a shrink-formable composition and defines an interior volume configured to enclose a component, such as a medical supply. The package may be formed by at least directing a flow of heated medium from a nozzle toward at least one region of the package precursor to cause the at least one region to shrink faster than an adjacent region of the package precursor. In some examples, an example system for shrink-forming a package includes the support and the nozzle.

16 Claims, 4 Drawing Sheets

SHRINK-FORMED PACKAGE

TECHNICAL FIELD

This disclosure relates to shrink-formed packages, for example, packages for medical supplies.

BACKGROUND

Packages, for example, packages for medical supplies such as medical devices, may be configured to protect the internal contents of the package from the external environmental and, in some cases, help protect the structural integrity of the internal contents. In addition, some medical packages are used to house medical supplies in a sterile environment.

SUMMARY

This disclosure describes packages and techniques for making packages. An example technique of forming a package includes retaining a package precursor in a support. The package precursor includes a shrink-formable composition and defines an interior volume configured to enclose a component, such as a medical supply. The package may be formed by at least directing a flow of heated medium from a nozzle toward at least one region (e.g., a corner, a region including folds, creases, pleats, or a region adjacent to a region having folds, creases, or pleats) of the package precursor to cause the at least one region to shrink faster than an adjacent region of the package precursor. Thus, a package formed using the example technique may define at least one selectively heat shrunk region that is more heat shrunk that an adjacent region. In some examples, an example system for shrink-forming a package includes the support and the nozzle.

In a first example, a method includes retaining a package precursor in a support, wherein the package precursor comprises a shrink-formable composition and defines an interior volume configured to enclose a medical supply, and directing a flow of heated medium from a nozzle toward at least one region of the package precursor to cause the at least one region to shrink to a greater extent than an adjacent region of the package precursor.

In a second example relating to the method of the first example, the package precursor defines at least one corner, folds, creases, or pleats, and the at least one region includes the at least one corner, folds, creases, or pleats.

In a third example relating to the method of the first or second examples, the nozzle is spaced from the at least one region of the package precursor by about 100 millimeters.

In a fourth example relating to the method of any of the first through third examples, directing the flow of heated medium toward the at least one region causes a temperature of the package precursor at or adjacent to the at least one corner to increase to about 200° C.

In a fifth example relating to the method of any of the first through fourth examples, directing the flow of heated medium toward the at least one region comprises directing the flow of the heated medium along a plurality of passes along a surface of the package precursor.

In a sixth example relating to the method of the fifth example, each pass of the plurality of passes has a speed of about 33 millimeters per second.

In a seventh example relating to the method of any of the first through sixth examples, the method further comprises, prior to directing the flow of heated medium toward the at least one region, shielding a non-shrink region of the package precursor from the flow of heated medium.

In an eighth example relating to the method of any of the first through seventh examples, the method further comprises, prior to directing the flow of heated medium toward the at least one region, shielding the adjacent region of the package precursor from the flow of heated medium.

In a ninth example relating to the method of any of the first through eighth examples, the package precursor comprises a sterilization window comprising a gas-permeable panel through which a sterilizing gas may pass into the interior volume of the package precursor, the method further comprising introducing the sterilizing gas through the gas-permeable panel into the interior volume defined by the package precursor.

In a tenth example relating to the method of the ninth example, the gas-permeable panel comprises a non-woven spun-bonded polymer fabric.

In an eleventh example, a system comprises a support configured to retain a package precursor comprising a shrink-formable composition, wherein the package precursor defines an interior volume enclosing a medical supply; and a nozzle configured to direct a flow of heated medium toward at least one region of the package to cause the at least one region to shrink to a greater extent than an adjacent region of the package precursor.

In a twelfth example relating to the system of the eleventh example, the system further comprises the package precursor defining at least one corner, folds, creases, or pleats, wherein the at least one region includes the at least one corner, folds, creases, or pleats.

In a thirteenth example relating to the system of the twelfth example, the nozzle is spaced from the package precursor by about 100 millimeters.

In a fourteenth example relating to the system of the twelfth or thirteenth examples, the nozzle is configured to direct the flow of heated medium to cause a temperature of the package precursor at or adjacent the at least one corner to increase to about 200° C.

In a fifteenth example relating to the system of any of the eleventh through fourteenth examples, the nozzle is configured to direct the flow of heated medium along a plurality of passes along a surface of the package precursor.

In a sixteenth example relating to the system of the fifteenth example, each pass of the plurality of passes has a speed of about 33 millimeters per second.

In a seventeenth example relating to the system of any of the eleventh through sixteenth examples, the system further comprises a shield configured to shield a region of the package precursor from the flow of heated medium.

In an eighteenth example relating to the system of the seventeenth example, the package precursor is configured to receive a medical supply, the shield being configured to hold the medical supply in place relative to the support.

In a nineteenth example relating to the system of any of the eleventh through eighteenth examples, the package precursor comprises a sterilization window comprising a gas-permeable panel through which a sterilizing gas may pass into the interior volume of the package precursor, the system further comprising a gas source configured to introduce the sterilizing gas through the gas-permeable panel into the interior volume defined by the package precursor.

In a twentieth example, a medical supply package comprises a package defining at least one heat shrunk corner, the package defining an interior volume and including a sterilization window comprising a gas-permeable panel through which a sterilizing gas may pass into the interior volume; and a medical supply in the interior volume of the package.

In a twenty-first example relating to the twentieth example, a region of the package adjacent to the at least one heat shrunk corner is not heat shrunk.

The details of one or more examples are set forth in the accompanying drawings and the description below. Other features, objects, and advantages will be apparent from the description and drawings, and from the claims.

DETAILED DESCRIPTION

This disclosure describes systems and techniques for shrink-forming a package from a package precursor, as well as packages having one or more structural features that help maintain the integrity of the package during storage and/or handling. The package precursor includes a shrink-formable composition. In some examples, a nozzle may direct a flow of heated medium (e.g., air or another fluid) toward at least one region of the package precursor to cause the at least one region to shrink relatively faster or to a greater extent than an adjacent region of the package precursor. The resulting package may therefore define at least one selectively heat shrunk region, which, as discussed below, is a structural feature that can help maintain the integrity of the package during distribution (e.g., during storage and handling).

The region of the package precursor that is shrunk faster than or to a greater extent than an adjacent region of the package precursor can include, for example, a corner of the package precursor and/or a part of the package precursor defining folds, creases, pleats, or other gathering of excess material (not needed to define an interior volume sufficient to enclose a component). In examples in which the region includes a corner, the techniques for forming a package described herein may cause a relatively sharp corner of the package precursor to be rounded or more otherwise rendered more blunt by shrink-forming the corner into the relatively more blunt region.

In other examples, the region of the package precursor that is shrunk faster than or to a greater extent than an adjacent region of the package precursor includes a region adjacent to a region having folds, creases, pleats, or other gathering of excess material. Heat shrinking this type of region may cause the excess material in an adjacent region to gather to a lesser extent due to the pulling of the package precursor material away from the folds, creases, pleats, or other gathering of excess material.

Transforming a sharp corner of a package precursor into a more blunt or rounded region or reducing the folds, creases, pleats, or other gathering of excess material at a region of the package precursor may promote the integrity of the resulting package, for example, by reducing the possibility that the package will tear or deform at the corner or other region during storage, e.g., when the package is housed in a more rigid container (e.g., a box), and/or during handling and distribution. In this way, the packages and techniques for forming a package described herein can help maintain the ability of the package to protect the internal contents of the package from environmental contaminants.

The internal contents of packages described herein can be any suitable component, such as, but not limited to, a medical supply. Thus, while medical supplies are primarily referred to throughout the disclosure, in other examples, the packages described herein may be used to house other types of components. Because of the nature of some medical packages, which in addition to helping to protect the medical supply during handling or storage, may help preserve the sterility of medical supply to the time of use, the packages, systems, and techniques described herein may be particularly advantageous when used with medical packages. By configuring a package to reduce the possibility that the package will tear, the packages, systems, and techniques for forming a package described herein can help maintain sterility of a medical supply enclosed in the package until use.

A medical package may house a medical supply within a sealed space or a breathable space, and the medical package, including the medical supply, may be sterilized prior to distribution. For example, the package may be exposed to a sterilization temperature at which a medical supply may be sterilized. In some examples, a package precursor described herein defines a sterilization window comprising a gas-permeable panel through which a sterilizing gas may pass into the interior volume of the package precursor (or resulting package). A sterilizing gas (e.g., ethylene oxide) may be introduced through the gas-permeable panel to sterilize the medical supply enclosed in the package.

A package, such as a flexible polymeric pouch, can be used to contain one or more components, such as medical devices. There may be a spatial dissimilarity between the shape of the interior volume defined by the package and the component being housed therein. This mismatch in geometric shape may result in excess packaging material at certain regions of the package, such as at the corners. A relatively large package may need to be used to house a relatively small component in order to accommodate the shape of the component. For example, if a flat pouch (e.g., in an envelope shape) is used to package a medical supply having a cylindrical or other three-dimensional shape (e.g., rectangular cuboid-shaped component), then there may be excess packaging material at the corners due to the geometric incompatibility between three-dimensional package contents and the relatively flat pouch.

In some cases, after a medical supply is housed in a package, the package is housed in a more rigid container, e.g., in a box-like carton, for shipping and storage. A single package may be stored in a carton or a plurality of packages may be stored in a box for distribution.

When a package having excess material at a particular region (e.g., one or more corners) is housed in a more rigid container, the excess material may define a point of early failure for the package. In some cases, this may due to creases (e.g., compound folds, gathering, or pleats of the packaging material) defined by the excess material and/or the excess material rubbing against the box. Abrasion of the package at the region with the excess material may cause a resulting breach in the environmental barrier after shipping and storage. In the case of sterile package, the abrasion of the package at the region with the excess material may compromise the sterility of the medical supply housed in the package.

The systems and techniques described herein are configured to reduce the excess material at the corners or other regions of a package. Thus, the resulting packages described herein that include one or more selectively heat shrunk regions may have blunt corners (e.g., rounded corners), or an otherwise reduce amount of packaging material at certain regions compared to other packages housing the same component. Directed and selective heat shrinking of a package precursor may help eliminate excess material at certain regions of the package, e.g., helping to reduce or eliminate sharp corners that may become points of failure, as discussed above. In addition, in cases in which a plurality of packages are boxed together without individual unit cartons protecting the package, the reduction or elimination of relatively sharp corners or other relatively sharp surfaces by selective heat shrinking may help reduce the possibility that the sharp corners may inadvertently puncture adjacent packages during distribution and storage.

In some cases, it may be undesirable to have a package in a snug fit with the component housed therein (e.g., directly adjacent to the component). For example, the snug fit may prevent a sterilizing gas from being sufficiently introduced into the interior volume of the package to sterilize the component. The packages described herein are not fully heat shrunk around the packaged component to define a package that is in direct contact with the component, but, rather, selected regions (e.g., one or more corners) of the package are selectively heat shrunk to reduce excess material at regions of the package, e.g., portions that may contain stress inducing contours. Selective and controlled heat shrinking of the package may help create a package that has a more protective and efficient volume to the component, but still enables a sterilizing gas to be introduced into the interior volume of the package and allow effective removal of the component at time of use. The smaller, more efficient package size may result in a more efficient sterilization process, thereby resulting in a cost savings.

In addition to helping to maintain the integrity of the packaging during storage and handling, as well as helping to maintain the sterility of the package components (if applicable), the packages, systems, and techniques described herein may reduce material cost used for packaging a component, e.g., due to the ability to use a smaller carton for housing the package. The smaller carton may also enable the packages to be arranged in a higher density, which may result in savings in transportation and storage, e.g., because more product can be stored on a pallet.

Figure 1:
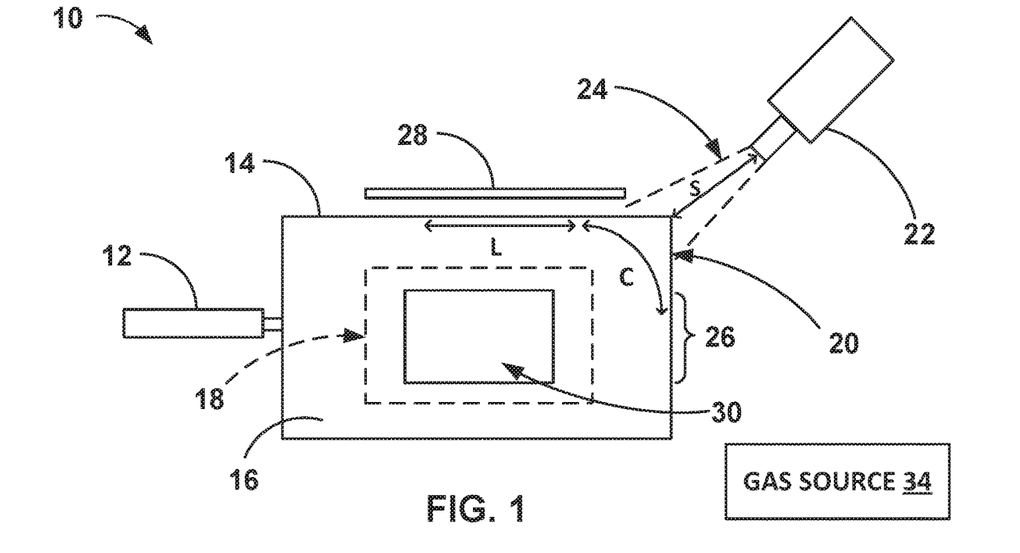
FIG. 1 is a conceptual diagram illustrating a top view of an example system including a support and a shrink-formable package precursor.

FIG. 1 is a conceptual diagram illustrating a top view of an example system 10 including a support 12 and a shrink-formable package precursor 14. The system 10 may be used for shrink-forming a package from the package precursor 14.

The support 12 is configured to retain the package precursor 14, e.g., hold the package precursor 14 in place during the shrink forming process used to define the package eventually formed from the precursor 14. The support 12 may include any suitable structure configured to hold the precursor 14 in place relative to a nozzle 22 or otherwise support the package precursor 14, such as, but not limited to, a clip, a fastener, a frame, or a housing. In some examples, the support 12 may define a relatively flat (e.g., planar) surface, for example, a platform or a belt, on which the precursor 14 is held stationary or is moved relative to the nozzle 22 at a predetermined speed.

The package precursor 14 is formed at least partially from or entirely from a shrink-formable composition. The shrink-formable composition may include one or more polymers. In some examples, the shrink-formable composition includes one or more of polyolefins, polyvinylchloride, polyesters, vinyl acetates, or mixtures, blends, or copolymers thereof. In some examples, the shrink-formable composition includes an Isoflex shrinkfilm, for example, Isoflex 46369 17B (Sigma Plastics Group, Chicago, Ill.).

In some examples, the package precursor 14 also includes a material through which a sterilizing gas can pass through into the interior volume 16 of the package precursor 14 and the package that is formed using the package precursor 14 and through which air may escape the interior volume 16 during the sterilization and during heat shrinking of regions of the package precursor 14. This material can define, for example, a sterilization window 30. As an example, the material can be a non-woven spun-bonded polymer material, such as, but not limited to, a spunbonded olefin sheet product, such as Tyvek® (Dupont, Wilmington, Del.), or sheets of other polymers, for example, polyethylene, or nylon. The material can be coupled to the shrink-formable composition using any suitable technique, such as, but not limited to, thermal sealing or ultrasonic welding.

The gas-permeable panel can be attached to the heat shrinkable material of the package precursor using any suitable technique, such as by heat sealing or adhering the gas-permeable panel to the heat shrinkable material. The heat shrinkable material and the gas-permeable panel can overlap by any suitable amount desired to secure the attachment thereof. In some examples, there is an overlap of about 5 cm to about 25 cm, such as about 10 cm to about 20 cm, between the gas-permeable panel and the heat shrinkable material.

The heat shrinkable material shrinks (e.g., decreases in surface area) more than the gas-permeable panel material in response to the same heating conditions. Thus, the gas-permeable panel (and window 30) may be positioned outside of the regions that are intended to be heat shrinkable. In some examples, the gas-permeable panel is not heat shrinkable.

Figure 2A:
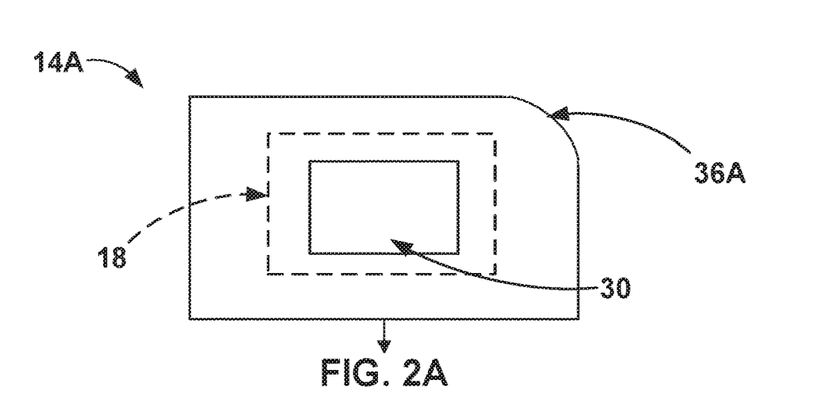
FIG. 2A is a conceptual diagram illustrating a top view of a first shrunk configuration of the package precursor of FIG. 1 with at least one region heat shrunk to shrunk to define a blunt (e.g., rounded) region.

The sterilization window 30 may have any suitable shape, such as, but not limited, to the rectangular shape shown in FIG. 2A, a circular shape, an ellipsoidal shape, a square shape, any shape defined by a closed curve, any closed polygon or rounded polygon shape, or composites or combinations thereof. A sterilization window 30 having rounded corners may help reduce stresses on the sterilization window 30 when one or more regions of the package precursor 14 are heat shrunk compared to a sterilization window 30 having sharp (e.g., right angle) corners because the rounded corners may help better distribute the stress along a larger area of the seal between the material defining sterilization window 30 and the heat shrinkable material of the package precursor 14. In addition, the sterilization window 30 can be located at any suitable place on the package precursor 14.

The package precursor 14 defines an interior volume 16 configured to enclose one or more contents, such as, but not limited to, a medical supply 18. Example medical supplies 18 include catheters, ablation medical devices, stents, or other medical devices. The package precursor 14 may have any suitable shape and contour configured to enclose the medical supply 18. After the package is formed using the package precursor 14, a shape and contour of the interior volume 16 may complement the medical supply 18 or at least better complement the medical supply 18 compared to if one or more regions (e.g., corners) of the package precursor 14 were not selectively heat shrunk to form the package. In some examples, the package precursor 14 defines a pouch (e.g., an envelope) or a pillow shape.

The package precursor 14 defines at least one corner 20. For example, the package precursor 14 may define a pouch defining four corners. In other examples, the package precursor 14 may define one, two, three, four or more corners. At least one corner 20 may be defined by one or more sealed peripheral edges of the package precursor 14. In the initial configuration of the package precursor 14, at least one corner 20 may protrude or extend the furthest from a geometric center of the package precursor 14 compared to other regions of the package precursor 14. Such protrusion or extension of the corner 20, or rigidity of the corner 20 imparted by sealed regions may cause the corner 20 or an adjacent region 26 to be susceptible to rupture, deformation, tearing, or otherwise lose integrity. To promote integrity of the package formed from the package precursor 14, the at least one corner 20 may be shrunk-formed into a blunt or rounded region, for example, by heat-treatment.

While the one or more regions of the package precursor 14 that are selectively heat shrunk are primarily described with reference to FIGS. 1-3C as being the corners 20 of the package precursor 14, in other examples, the one or more regions of the package precursor 14 that are selectively heat shrunk can be another region of the package precursor 14, e.g., a region that defines pleats, folds, creases, or other gathering of excess packaging material after the medical supply 18 is introduced in the package precursor 14, or a region of the package precursor 14 adjacent to the pleats, folds, creases, or other gathering of excess packaging material. Thus, in other examples, instead of selectively heat shrinking the corners, a region adjacent to a corner 20 can be selectively heat shrunk using the methods and systems described herein. Selective heat shrinking of one or more regions of package precursor 14 may help reduce the excess material at the region or an adjacent region, thereby reducing potential points of failure for the resulting package, as discussed above.

The system 10 includes a nozzle 22 configured to directing a flow of heated medium 24 toward at least one corner 20 to form the package by causing the least one corner 20 to shrink to a greater extent than an adjacent region 26 of the package precursor 14. In some examples, the nozzle 22 may include a heat gun, and the heated medium 24 includes heated air or another fluid. The nozzle 22 is configured to direct flow of heated medium 24 toward a predetermined region of the package precursor 14. For example, the nozzle 22 may be configured to direct flow of heated medium 24 in a static pattern, or in a moving pattern. In some examples, the nozzle 22 is configured to direct flow of heated medium 24 along a plurality of passes along a surface of the package precursor 14. The plurality of passes may include linear passes (for example a linear pass L shown in FIG. 1), or curved passes (for example, a curved pass C shown in FIG. 1). In some examples, each pass of the plurality of passes has a speed of about 33 millimeters (mm) per second.

In some examples, nozzle 22, for example, an opening from which flow of the heated medium 24 originates, is spaced from the package precursor 14 by a predetermined spacing S. For example, the spacing S may be defined between the nozzle 22 and the region of the package precursor 14 that is being heat shrunk. If the spacing S is relatively lower, a temperature of a region at which flow of heated medium 24 is directed may be relatively higher, and vice versa. In some examples, the spacing S is about 100 mm.

In some examples, the nozzle 22 is configured to direct flow of heated medium 24 to cause a temperature of the package precursor 14 at or adjacent the corner 20 to reach a predetermined temperature. The predetermined temperature may cause heat shrinkable material of the package precursor 14 at the corner 20 (or other selected region) to be heat shrunk to shrink, for example, at a faster rate than or to a relatively greater extent that an adjacent region 26. In some examples, the predetermined temperature is about 200° C.

In some examples, the system 10 includes a shield 28 configured to shield a non-shrink region of the package precursor 14 or a region of the package precursor 14 that is not intended to be heat shrunk from flow of the heated medium 24. The shield 28 may be isolated from the support 12 or may be defined by a portion of the support 12, or may be joined to, adhered to, welded to, or supported by the support 12. The non-shrink region may include an adjacent region 26 or another region of the package precursor 14. In some examples, the non-shrink region may include more than one connected or distinct regions, and the shield 28 may include a single shield or multiple shield portions configured to shield respective non-shrink regions of the package precursor 14.

In some examples, the system 10 further includes a gas source 34 configured to introduce a sterilizing gas through the sterilization window 30 into the interior volume 16 defined by the package precursor 14. The sterilizing gas may include one or more of ethylene oxide, steam, or another sterilizing component or combinations thereof.

The package precursor 14 may be heat-treated to form the package, for example, by shrink-forming one or more selected regions of the package precursor 14 and not the entire package precursor 14. FIG. 2A is a conceptual diagram illustrating a top view of a first shrunk configuration 14A of the package precursor 14 of FIG. 1 with at least one corner 20 shrunk to define a rounded region 36A. For example, the nozzle 22 may direct flow of a heated medium 24 towards the corner 20 to shrink the corner 20 into the more blunt or rounded region 36A. More corners of package precursor 14 may be subsequently rounded.

Figure 2B:
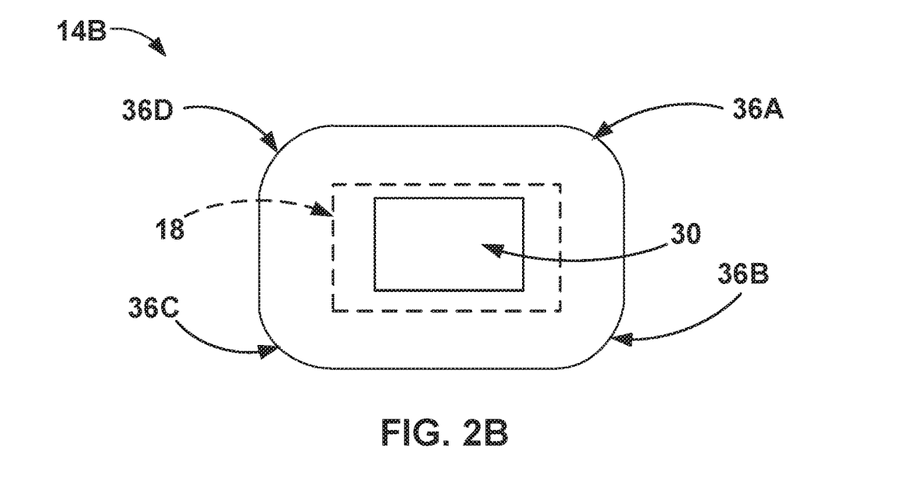
FIG. 2B is a conceptual diagram illustrating a top view of a second heat shrunk configuration of the package precursor with all corners heat shrunk to define a package including blunt regions.

FIG. 2B is a conceptual diagram illustrating a top view of a second shrunk configuration 14B of the package precursor 14 with all corners shrunk to define a rounded package including rounded regions 36A to 36D. The rounded regions 36A to 36D may exhibit a lower susceptibility to rupture, tearing, or damage, and may be able to sustain stresses while retaining integrity of the package formed from package precursor 14. In some examples, the package includes the second shrunk configuration 14B. Such a package may be able to house the medical supply 18 defining three-dimensional protrusions or features or a bulky exterior, while maintaining the integrity of the package.

Figure 3A:
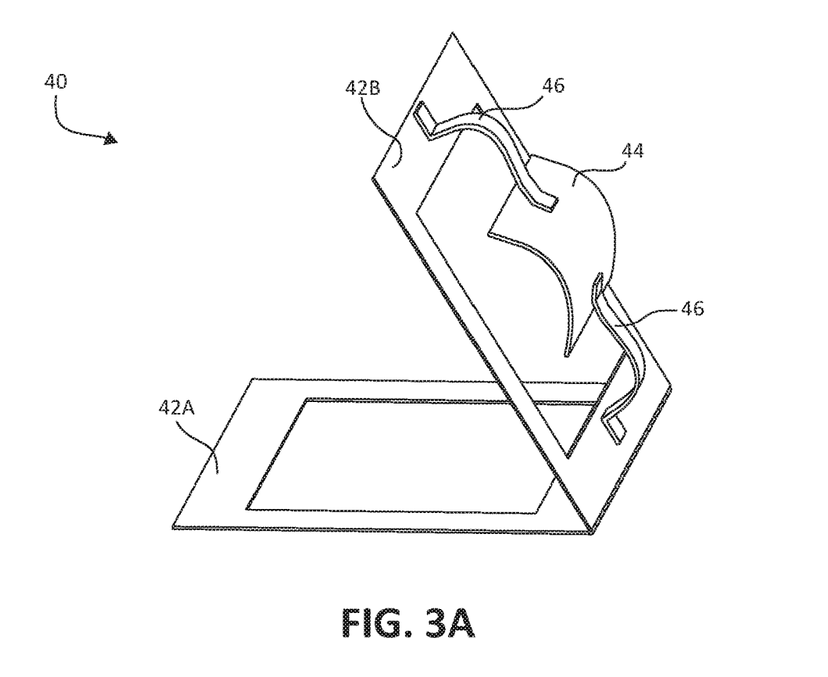
FIG. 3A illustrates a perspective view of an example support configured to retain a shrink-formable package precursor.
Figure 3B:
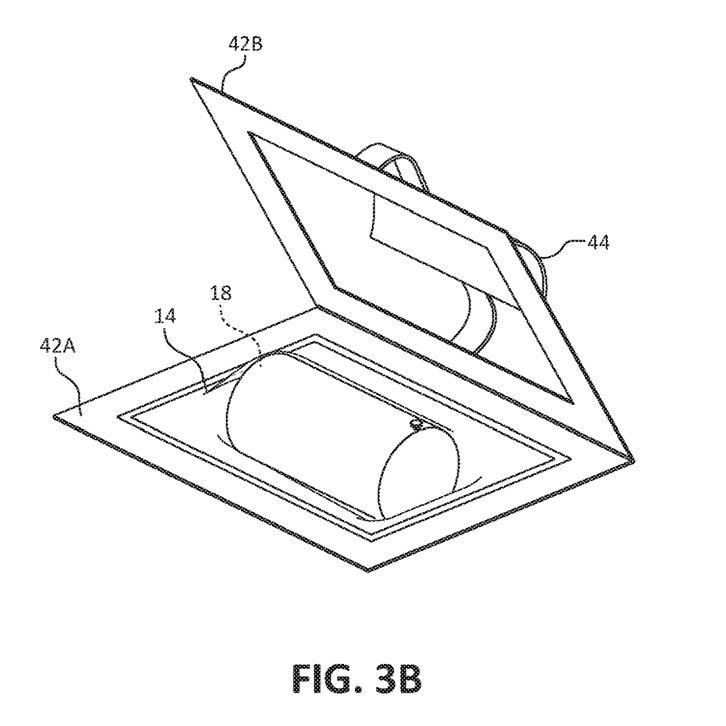
FIGS. 3B and 3C illustrate the support of FIG. 3A in combination with an example shrink-formable package precursor and an example component intended to be packaged within an interior volume of a package formed from the shrink-formable package precursor.
Figure 3C:
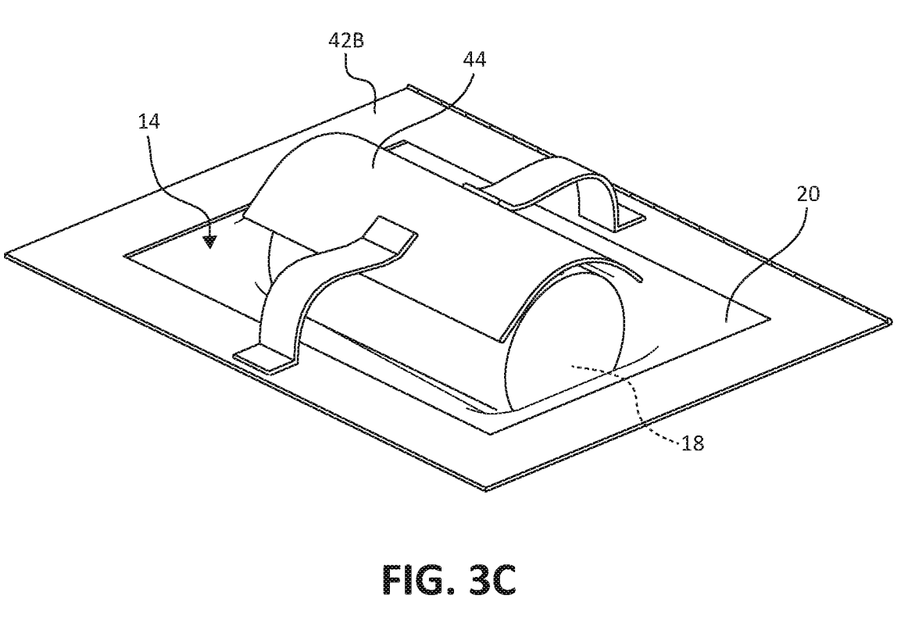

In some examples, the support 12 includes a frame that defines the shield 28 that is configured to isolate regions of the package precursor 14 that is not intended to be heat shrunk from the heated medium 24. FIG. 3A illustrates a perspective view of an example support 40 configured to retain the shrink-formable package precursor 14. The support 40 is an example of the support 12 shown in FIG. 1. FIGS. 3B and 3C illustrate the support of FIG. 3A in combination with the package precursor 14 and the medical supply 18 introduced and sealed within the interior volume 16 of the package precursor 14.

The example support 40 includes a first frame member 42A and a second frame member 42B that are movable relative to each other. For example, the frame members 42A, 42B can be mechanically connected to each other via a hinge or other mechanical joint, or may be formed from an integral piece of material that is folded to define the frame members 42A, 42B. When the frame members 42A, 42B are spaced from each other, as shown in FIGS. 3A and 3B, the frame members 42A, 42B are in an open state. In the open state, the frame members 42A, 42B are positioned relative to each other to enable the package precursor 14 and the medical supply 18 to be inserted between the frame members 42A, 42B. The frame members 42A, 42B can be moved towards each other (such as by moving one or both frame members 42A, 4*b*) to define a closed state, as shown in FIG. 3C. In the closed state, the frame members 42A, 42B are positioned relative to each other to hold the package precursor 14 and the medical supply 18 in place between the frame members 42A, 42B.

When frame members 42A, 42B are in the closed state and the package precursor 14 and the medical supply 18 in place between the frame members 42A, 42B, the one or more regions of the package precursor that are to be heat shrunk (e.g., the corner 20) are exposed to enable the heated medium 24 to reach the one or more regions.

The frame members 42A, 42B can be formed from any suitable material, such as, but not limited to, a polymer or another heat resistant material that is configured to maintain the integrity of the frame members 42A, 42B in the presence of the heated medium 24. The frame members 42A, 42B may be cooled between heat shrinking operations of different package precursors 14.

In some examples, the support 40 also includes a shield 44 that is configured to cover portions of the package precursor 14 that are not intended to be heat shrunk and help prevent those portions from heat shrinking in response to the application of the heated medium 24 to the package precursor 14. The shield 44 is an example of the shield 28 of FIG. 1 and may be formed from any suitable material, such as a material configured to absorb or reflect heat from the heated medium 24 to help prevent the portions of the package precursor 14 under the shield 44 from heat shrinking.

In some examples, the shield 44 is configured to reflect heat from areas not intended to be shrunk. Additionally, the shield 44 may also be configured to stabilize the medical supply 18 within the package precursor 14 and help ensure the medical supply 18 is placed in the desired location within the package precursor 14 and does not shift during processing. That is, the shield 44 may help hold the medical supply 18 in place relative to the package precursor 14 and/or relative to the frame members 42A, 42B. For example, as shown in FIGS. 3A-3C, the shield 44 can define a profile that corresponds to the contour of the medical supply 18, such that when the frame members 42A, 42B are in a closed state (FIG. 3C), the shield 44 mates with the medical supply 18 in a relatively close fit. The one or more the regions of the package precursor 14 that are to be heat shrunk to reduce the amount of packaging material at the regions (e.g., to define a more blunt or rounded corner 36A) may depend on the location of the medical supply within the interior volume 16. For example, if the medical supply is not centered within the interior volume 16, then two or three corners of the package precursor 14 may have more excess material than at least one other corner of the package precursor 14. Thus, a shield 44 that is configured to hold medical supply 18 in place relative to the package precursor 14 may help ensure that the regions of the package precursor 14 that are to be heat shrunk are well defined and do not change as the medical supply 18 moves within the interior volume 14.

The shield 44 can be connected to the frame members 42A, 42B using any suitable technique, such as via the bands 46 as shown in FIGS. 3A-3C, via an adhesive, welding, or the like. Alternatively, the shield 44 can be integrally formed with the frame member 42B. The bands 46 can be rigid or flexible. Although the shield 44 is shown on only one frame member 42B, in other examples, the other frame member 42A may include a similar shield.

Figure 4:
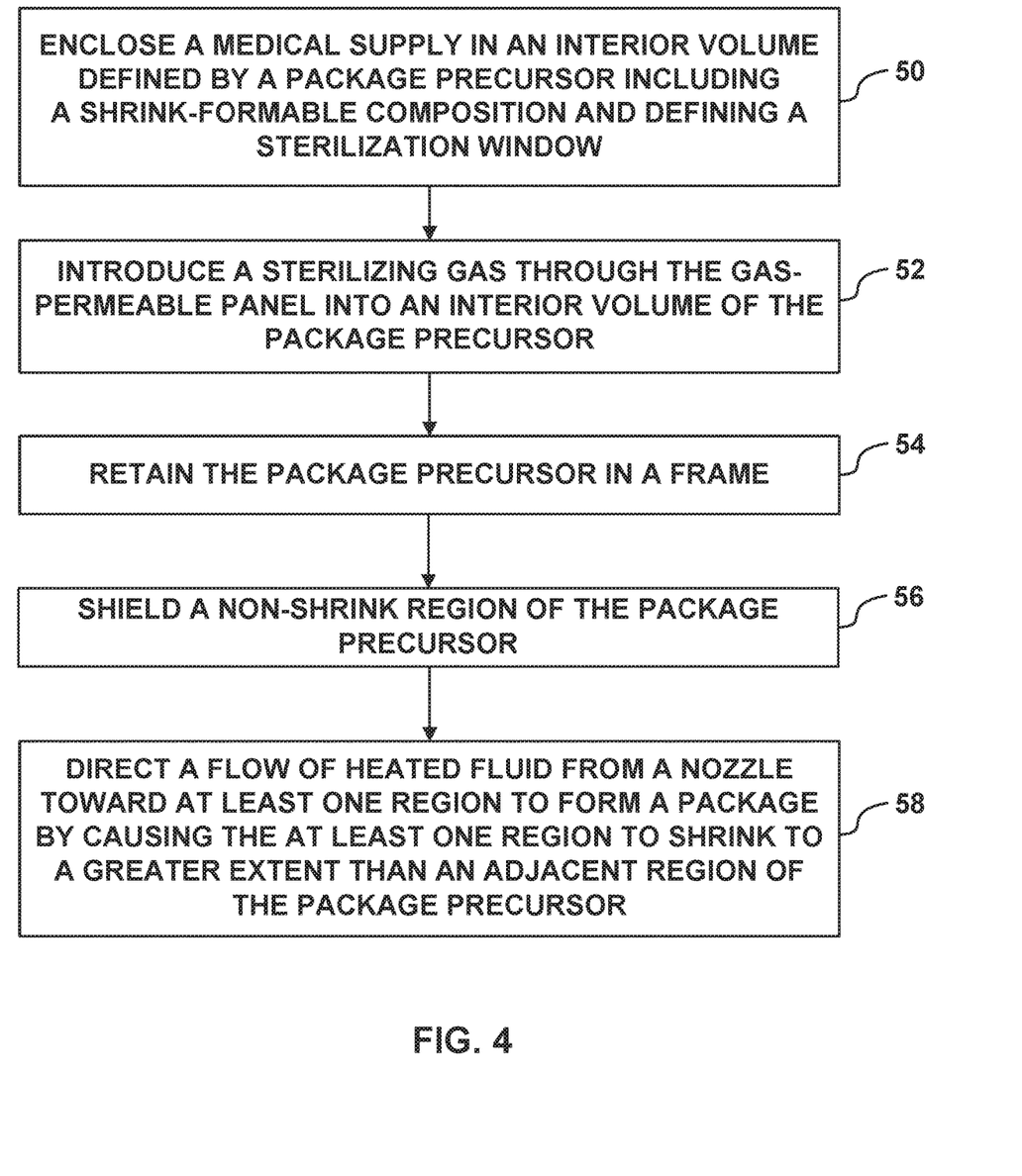
FIG. 4 is a flow diagram illustrating an example technique for shrink-forming a package.

FIG. 4 is a flow diagram illustrating an example technique for shrink-forming a package. While the example technique of FIG. 4 is described with reference to example system 10 of FIG. 1 and the precursor package 14, 14A, and 14B of FIGS. 1, 2A, and 2B, the example technique of FIG. 4 may be used to transform any package precursor according to the disclosure into a package using any suitable system.

The example technique of FIG. 4 includes enclosing a medical supply 18 in an interior volume 16 defined by a package precursor 14 (50). For example, a person or a machine can introduce the medical supply 18 into the package precursor 14 through an unsealed opening of package precursor 14 and then subsequently seal the opening. The package precursor 14 defines a sterilization window 30. In some examples, the example technique of FIG. 4 includes optionally forming the sterilization window 30 in the package precursor 14. For example, one or more regions of the package precursor 14 may be punched, stamped, machined, or otherwise cut to define an opening over which a gas-permeable panel may be positioned. The gas-permeable panel can be, for example, adhered to a surface surrounding the opening formed in the package precursor 14 with an adhesive composition, or by heat-sealing or welding a peripheral region of the gas-permeable panel to a surface of the package precursor 14.

In some examples, the example technique of FIG. 4 includes introducing a sterilizing gas through the sterilization window 30 into the interior volume 16 defined by package precursor 14 (52). For example, the sterilizing gas may be introduced from the gas source 34, for example, via a fluid conduit, or any fluid connection.

The example technique of FIG. 4 further includes retaining the package precursor 14 in a support 12 (54). For example, the package precursor 14 can be positioned on a surface defined by the support 12 and/or held in a clip, fastener, or another mechanism of support 12.

In an initial configuration (for example, the configuration shown in FIG. 1), the package precursor 14 includes a shrink-formable composition and defines at least one corner 20. In some examples, the example technique of FIG. 4 includes shielding a non-shrink region of the package precursor 14 from flow of heated medium 24 (56). For example, one or more shields 28 may be positioned adjacent respective non-shrink regions. The non-shrink regions may include region 26 adjacent to the corner 20 (or other region) to be heat shrunk, or another region of package precursor 14. In some examples, the non-shrink region includes the sterilization window 30.

A flow of heated medium 24 is directed from the nozzle 22 toward at least one corner 20 or other non-corner region to form a package by causing the at least one corner 20 or other region to shrink to a greater extent than adjacent region 26 of package precursor 14 (58). In some examples, the corner 20 or other region to be heat shrunk exhibits a 10% to 20% reduction in surface area due to the selective and preferential heat shrinking of the corner 20 (or other region). If the region to be selectively heat shrunk includes a corner 20 of the package precursor 14, then the heated medium 24 causes the corner 20 to shrink to define rounded region 36A (FIGS. 2A and 2B). The heated medium 24 can be directed to other corners (or other non-corner regions) of the package at the same time as or at different times than the corner 20 to define, for example, respective rounded regions 36A to 36D (or fewer rounded regions than four or greater rounded regions than four). The heated medium 24 may be directed to the selected regions of the package precursor 14 using any suitable technique, such as by directing flow of the heated medium 24 along a plurality of passes (linear passes L, curved passes C, or combinations thereof) along a surface of the package precursor 14. In some examples, each pass of the plurality of passes has a speed of about 33 mm per second.

In some examples, the nozzle 22 is spaced from package precursor 14, for example, from at least one corner 20 by about 100 mm while the heated medium 24 is directed to the one or more corners of the package precursor 14. In addition, the temperature of the heated medium 24 is selected to cause a temperature of the selected region of the package precursor 14 (e.g., at or adjacent at least one corner 20) to increase to about 200° C.

In some examples of the technique described herein, the one or more regions of the package precursor 14 are heat shrunk (58) prior to introducing the medical supply 18 into the interior volume 16 of the package precursor 14. This may be referred to as pre-shrinking of the package precursor 14 and can be used to define the package instead of the selective heat shrinking after the medical supply 18 into the interior volume 16 of the package precursor 14.

Various examples of the disclosure have been described. Any combination of the described systems, operations, or functions is contemplated. These and other examples are within the scope of the following claims.

What is claimed is:

1. A method comprising:
   introducing a medical supply into an interior volume defined by a flexible polymeric pouch through an opening defined by the flexible polymeric pouch;
   retaining the flexible polymeric pouch in a support, wherein the flexible polymeric pouch comprises a shrink-formable composition; and
   directing a flow of heated medium from a nozzle toward at least one region of the flexible polymeric pouch to cause the at least one region to shrink to a greater extent than an adjacent region of the flexible polymeric pouch,
   wherein prior to directing the flow of heated medium toward the at least one region, the method comprises shielding a non-shrink region of the flexible polymeric pouch or the adjacent region of the flexible polymeric pouch from the flow of heated medium.

2. The method of claim 1, wherein the flexible polymeric pouch defines at least one corner, folds, creases, or pleats, and the at least one region includes the at least one corner, folds, creases, or pleats, and wherein directing the flow of heated medium from the nozzle toward the at least one region comprises directing the flow of heated medium toward the at least one corner, folds, creases, or pleats to shrink the at least one corner, folds, creases, or pleats to a greater extent than an adjacent region of the flexible polymeric pouch and reduce an amount of pouch material at the at least one corner, folds, creases, or pleats.

3. The method of claim 1, wherein the nozzle is spaced from the at least one region of the flexible polymeric pouch by about 100 millimeters.

4. The method of claim 1, wherein directing the flow of heated medium toward the at least one region causes a temperature of the flexible polymeric pouch at or adjacent to the at least one region to increase to about 200° C.

5. The method of claim 1, wherein directing the flow of heated medium toward the at least one region comprises directing the flow of the heated medium along a plurality of passes along a surface of the flexible polymeric pouch.

6. The method of claim 5, wherein each pass of the plurality of passes has a speed of about 33 millimeters per second.

7. The method of claim 1, wherein the flexible polymeric pouch comprises a sterilization window comprising a gas-permeable panel through which a sterilizing gas may pass into the interior volume of the flexible polymeric pouch, the method further comprising introducing the sterilizing gas through the gas-permeable panel into the interior volume.

8. The method of claim 7, wherein the gas-permeable panel comprises a non-woven spun-bonded polymer fabric.

9. The method of claim 1, wherein the flexible polymeric pouch has an envelope configuration.

10. A system comprising:
    a support configured to retain a flexible polymeric pouch comprising a shrink-formable composition, wherein the flexible polymeric pouch defines an interior volume enclosing a medical supply;
    a nozzle configured to direct a flow of heated medium toward at least one region of the flexible polymeric pouch to cause the at least one region to shrink to a greater extent than an adjacent region of the flexible polymeric pouch; and
    a shield configured to shield at least part of the flexible polymeric pouch from the flow of heated medium.

11. The system of claim 10, further comprising the flexible polymeric pouch defining at least one corner, folds, creases, or pleats, wherein the at least one region includes the at least one corner, folds, creases, or pleats, and wherein the flow of heated medium is configured to shrink the at least one corner, folds, creases, or pleats to a greater extent than an adjacent region of the flexible polymeric pouch and reduce an amount of pouch material at the at least one corner, folds, creases, or pleats.

12. The system of claim 11, wherein the nozzle is spaced from the flexible polymeric pouch by about 100 millimeters.

13. The system of claim 11, wherein the nozzle is configured to direct the flow of heated medium to cause a temperature of the flexible polymeric pouch at or adjacent the at least one region to increase to about 200° C.

14. The system of claim 10, wherein the nozzle is configured to direct the flow of heated medium along a plurality of passes along a surface of the flexible polymeric pouch.

15. The system of claim 10, the shield being configured to hold the medical supply in place relative to the support.

16. The system of claim 10, wherein the flexible polymeric pouch comprises a sterilization window comprising a gas-permeable panel through which a sterilizing gas may pass into the interior volume of the flexible polymeric pouch, the system further comprising a gas source configured to introduce the sterilizing gas through the gas-permeable panel into the interior volume.

* * * * *